US007731575B2

(12) United States Patent
Ozil

(10) Patent No.: US 7,731,575 B2
(45) Date of Patent: Jun. 8, 2010

(54) VENTILATION UNIT WHICH CAN BE DRESSED LIKE A TIGHT SUIT OR SIMILAR

(75) Inventor: Samuel Ozil, Rochefort du Gard (FR)

(73) Assignee: Delta Protection, Bagnols-sur-Ceze (FR)

( * ) Notice: Subject to any disclaimer, the term of this patent is extended or adjusted under 35 U.S.C. 154(b) by 457 days.

(21) Appl. No.: 10/537,294

(22) PCT Filed: Nov. 21, 2003

(86) PCT No.: PCT/FR03/03441

§ 371 (c)(1),
(2), (4) Date: Jun. 2, 2005

(87) PCT Pub. No.: WO2004/060088

PCT Pub. Date: Jul. 22, 2004

(65) Prior Publication Data

US 2006/0154594 A1 Jul. 13, 2006

(30) Foreign Application Priority Data

Dec. 6, 2002 (FR) .................................. 02 15404

(51) Int. Cl.
*A61M 16/00* (2006.01)

(52) U.S. Cl. ................................ 454/283; 128/205.22

(58) Field of Classification Search ................. 454/251, 454/254, 256, 257; 2/1, 81; 128/201-204; 126/201-204
See application file for complete search history.

(56) References Cited

U.S. PATENT DOCUMENTS 2,512,990 A * 6/1950 Akerman ......................... 2/81
2,989,049 A 6/1961 Jean-Philippe
3,045,243 A * 7/1962 Lash et al. ......................... 2/1
3,468,299 A 9/1969 Amato
4,821,709 A * 4/1989 Jensen .................. 128/204.21
5,577,496 A * 11/1996 Blackwood et al. .... 128/201.25
5,586,861 A * 12/1996 Berger ........................ 415/118
6,186,140 B1 * 2/2001 Hoague ................. 128/202.22

FOREIGN PATENT DOCUMENTS

| | | |
|---|---|---|
| AT | 393 086 | 8/1991 |
| CH | 671 340 | 8/1989 |
| FR | 2 515 048 | 4/1983 |
| GB | 935 934 | 9/1963 |
| WO | WO 01/52675 | 7/2001 |

* cited by examiner

*Primary Examiner*—Steven B McAllister
*Assistant Examiner*—Samantha A Miller
(74) *Attorney, Agent, or Firm*—Young & Thompson

(57) ABSTRACT

A ventilation unit includes a casing which has two openings and an electric connection passage, a filter cartridge, a turbine disposed inside the casing and having an input and an output and a motor, a duct linking the output to the outside area of the casing via the output, another casing with a passage created inside the wall, a control circuit and a source disposed inside the casing, elements for associating the two housings such that the passages form a single passage, a flow meter inside the duct. The control circuit includes an exit which can issue a first alarm signal when the electric energy value of the source falls below a threshold. The ventilation unit is suitable for the ventilation of nuclear protection suits, bacteriological protection suits or protective suits in hospital environments.

16 Claims, 1 Drawing Sheet

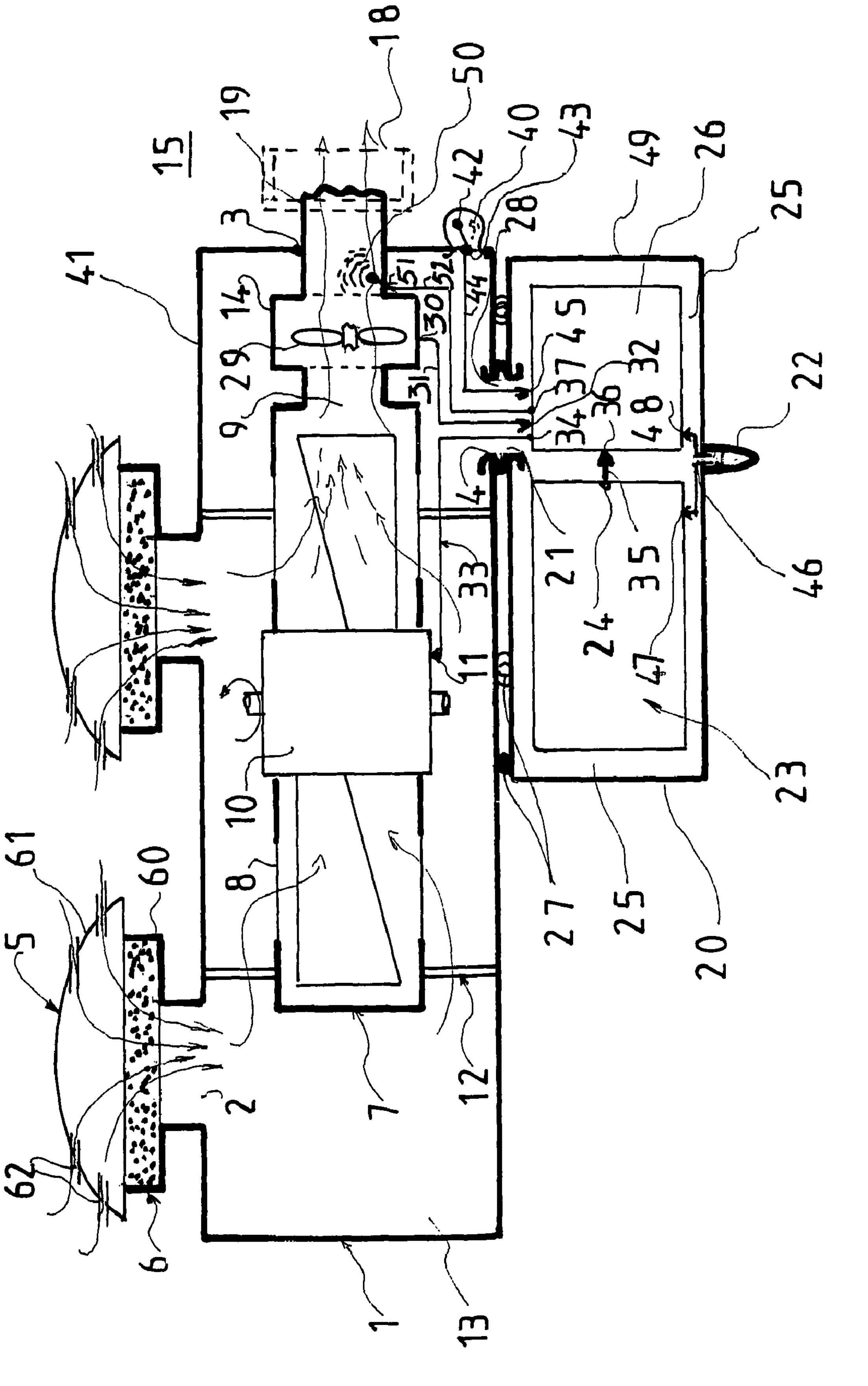

VENTILATION UNIT WHICH CAN BE DRESSED LIKE A TIGHT SUIT OR SIMILAR

FIELD OF THE INVENTION

The present invention relates to a ventilator units for garments such as pressure suits or the like, for the purpose of ventilating them with an ambient fluid such as air, and it finds a particularly advantageous application for ventilating the insides of antinuclear or antibacteriological confinement suits, for certain garments for providing protection in a hospital environment, for garments complying with standards that are applicable in particular in the nuclear, bacteriological, chemical, and biological, etc. fields, and even for garments for reducing thermal stress, etc. for example.

BACKGROUND OF THE INVENTION

Ventilator units already exist for ventilating garments such as pressure suits or the like with an ambient fluid, however they do not all satisfy operating conditions in the above-mentioned applications, or else they are of a structure that is not sufficiently compact to enable them to be made completely self-contained and easy to manufacture and to associate with the garments they are to ventilate, nor are they sufficiently simple to ensure that the operations required for maintenance are relatively easy.

OBJECT OF THE INVENTION

The present invention thus seeks to provide a ventilator unit for ventilating a garment such as pressure suit or the like with an ambient fluid, which unit mitigates to a considerable extent the above-mentioned drawbacks of devices known in this field in the prior art.

SUMMARY OF THE INVENTION

More precisely, the present invention provides a ventilator unit for ventilating the inside of a garment such as a pressure suit or the like with an ambient fluid, the unit being characterized by the fact that it comprises:

a first leaktight case having at least one inlet opening suitable for sucking in the fluid, and an outlet opening, and also a first electrical connection passage;

a filter cartridge;

means for mounting the filter cartridge in association with the inlet opening of the first case;

an impeller having at least one inlet port for sucking in the fluid contained in the first case, and an outlet orifice for delivering the sucked-in fluid, the impeller having a drive motor controllable via a power supply input;

means for mounting the impeller in the inside of the first case;

a duct for connecting the outlet orifice of the impeller to the outside of the first case, the duct passing in leaktight manner through the outlet opening of the first case;

a second case;

a second electrical connection passage made through the wall of the second case;

a source suitable for delivering electrical energy to an output terminal, the source being disposed in the inside of the second case;

an electronic control circuit;

means for associating the first and second cases in such a manner that the first and second electrical connection passages form a single leakproof third electrical connection passage;

a flow meter disposed inside the duct, the flow meter having an outlet suitable for delivering an electrical signal representative of the flow rate of fluid passing along the duct;

a first electrical connector for connecting the output of the flow meter to a first input of the electronic control circuit;

a second electrical connector for connecting a first control output of the electronic control circuit to the control input of the motor for driving the impeller; and a third electrical connector for connecting the electrical energy source to a power supply input of the electronic control circuit;

the electronic control circuit further including an output suitable for delivering a first alarm signal when the level of electrical energy delivered by the source drops below a determined threshold value.

According to another characteristic of the invention, the electronic control circuit is located inside the second case.

According to another characteristic of the invention, the ventilator unit includes a flow rate regulator circuit suitable for delivering a second alarm signal when the flow rate of fluid in the duct varies by a determined amount about a given nominal value for flow rate, the regulator circuit advantageously being situated in the first case, although it could be disposed in the second case.

BRIEF DESCRIPTION OF THE DRAWING

Other characteristics and advantages of the invention appear from the following description given with reference to the accompanying drawing by way of non-limiting illustration, in which drawing:

the sole FIGURE is a block diagram of an embodiment of a ventilator unit of the invention for ventilating the inside of a garment such as a pressure suit or the like by means of an ambient fluid.

The Applicant seeks to specify that the FIGURE shows only one embodiment of the invention, and that other embodiments can exist that satisfy the definition of the invention.

The Applicant also specifies that when, according to the definition of the invention, its subject matter comprises "at least one" element having some given function, the embodiment described may have a plurality of said elements.

The Applicant also specifies that if the embodiment of the invention as shown has a plurality of elements that are identical in function, and if in the description does not specify that the invention must necessarily have some particular number of said elements, then the invention can be defined as comprising "at least one" of said elements.

DETAILED DESCRIPTION OF THE INVENTION

With reference to the sole FIGURE, the ventilator unit of the invention for ventilating the inside of a garment such as a pressure suit or the like by means of an ambient fluid such as air comprises a first leaktight case 1 in the form either of a single part or of a plurality of parts that are assembled together, e.g. made of a casting of light metal such as aluminum or the like, or even, when possible, out of a hard plastics material. This first case 1 has at least one inlet opening 2 suitable for sucking in the ambient fluid, an outlet opening 3, and a first passage 4 for passing an electrical connection. In the embodiment shown, the ventilator unit has two inlet openings, and it is clear that it could have even more.

The ventilator unit further comprises a filter cartridge 5 and means 6 for mounting the filter cartridge 5 in association with the inlet opening 2 of the first case 1. By way of example, these means 6 are constituted, as shown, by a hollow housing formed in the wall 41 of the case 1 and suitable for having a portion of the cartridge plugged into it.

In one possible embodiment, and as shown, the filter cartridge 5 is constituted firstly by a filter pellet 60, e.g. for filtering first particles of a given size, the dimensions of the pellet enabling it to cover the entire inlet opening 2 of the first case, and secondly by a cap 61 covering the pellet 60 so that the pellet is situated between the cap and the inlet opening 2 of the first case, the cap including filter orifices 62 for filtering second particles of dimensions greater than those of the first particles, thereby constituting a first filter stage for filtering the ambient fluid.

However, the pellets may also be filter pellets for filtering chemicals or the like, in solid and/or gaseous form.

There is also provided an impeller 7 (two of its blades being shown diagrammatically), together with means 12 for mounting the impeller in the inside 13 of the first case 1.

The impeller includes at least one inlet port 8 for sucking in the fluid contained in the first case 1 and coming from the outside 15 of the first case via the inlet openings 2, the filter pellets 6, and the cap 5, and it also has an outlet orifice 9 for delivering the fluid sucked in via the inlet ports 8. In conventional manner, the impeller 7 has a drive motor 10 of electric or similar type, controllable from a power supply input 11.

The means 12 for mounting the impeller 17 inside the first case 1 are represented diagrammatically by spacers, however they could be of any other type, it being understood that they are functionally defined in such a manner that the impeller 7 is located in the inside 13 of the first case 1 substantially in the central portion thereof, and that the inlet ports 8 can suck in the fluid that is to be found in the inside 13 of the first case.

As shown, the ventilator unit also includes a duct 14 for connecting the outlet orifice 9 of the impeller 7 to the outside 15 of the first case 1, said duct 14 passing in leaktight manner through the outlet opening 3 of the first case, sealing being provided, for example, by a gasket or by welding, if necessary.

The ventilator unit further comprises a second case 20 and a second electrical connection passage 21 made through the wall 49 of said second case. This second case is advantageously made in the same manner as the first, e.g. as one or more parts for assembling together, made by casting a light metal such as aluminum or the like, or even, in certain circumstances where this is possible, a hard plastics material.

The ventilator unit of the invention further includes a source 23 suitable for delivering electrical energy via an output terminal 24, the source 23 being disposed inside the second case 20, said source being constituted, for example, by one or more rechargeable batteries.

The unit also includes an electronic control circuit 26 that is advantageously programmable, the electronic control circuit 26 preferably being disposed inside the second case 20.

Means 27, e.g. hooks or the like, shown diagrammatically, are also provided for associating the first and second cases 1 and 20 as described above so that the first and second electrical connection passages 4 and 21 constitute a single leaktight third passage 28 for passing electrical connections.

By way of example, this is achieved by the two passages 4 and 21 being bordered by respective O-rings or the like which, when the two cases are associated with each other, are pressed against each other with a certain amount of resilient force so as to form the above-described leaktight third passage 28.

The ventilator unit of the invention includes a flow meter 29 which is disposed most advantageously inside the duct 14. This flow meter is known in itself and has an output 30 suitable for delivering an electrical signal representative of the flow rate of fluid passing along the duct 14.

The ventilator unit has a first electrical connector 31 for connecting the output 30 of the flow meter 29 to a first input 32 of the electronic control circuit 26, a second electrical connector 33 for connecting a first control output 34 of the electronic control circuit 36 to the control input 11 of the drive motor for the impeller 10, and a third electrical connector 35 for connecting the output 24 of the electrical energy source 23 to a power supply input 36 of the electronic control circuit 26.

The electronic control circuit 26 also includes an output 37 suitable for delivering a first alarm signal when the electrical energy level delivered by the source 23 drops below a determined threshold value.

The ventilator unit also advantageously includes a flow rate regulator circuit suitable for delivering a second alarm signal when the flow rate of fluid in the duct 14 varies by a determined amount about a given nominal flow rate value which is determined for each garment that is to be ventilated and depends on the activity level expected of the person who is to wear the garment, said flow rate regulator circuit advantageously being situated in the first case 1, e.g. in association with the impeller 7, or more particularly its motor 10.

Nevertheless, it is clear that the flow rate regulator circuit could be located in the second case 20.

In the embodiment shown, in order to simplify the drawing accompanying the present description, the flow rate regulator circuit is shown as being located in the second case 20 and integrated with the electronic control circuit 26.

According to an advantageous characteristic of the invention, the ventilator unit further includes a switch 40 mounted to pass in leaktight manner through the wall 41 of the first case 1 so that its control element 42, such as a lever or the like, is accessible from the outside 15 of the first case 1, possibly even being protected in a flexible sheath, while its electrical control terminals 43 are situated on the inside 13 of the first case 1, the ventilator unit having a fourth electrical connector 44 for connecting the electrical control terminals 43 of the switch 40 to a general control input 45 of the electronic control circuit 26 in order to switch on and off the operation of the ventilator unit, as described below.

In preferred manner, the ventilator unit of the invention further includes an electrical connection pin 22 mounted in leaktight manner through the wall 49 of the second case 20, the pin having output terminals 46 situated on the inside 25 of said second case 20 and connected respectively to an input 47 for feeding energy to the energy source 23 and to a control input 48 of the electronic control circuit 26 for purposes that are explained below when describing the operation of the ventilator unit.

Also in highly preferred manner, the ventilator unit of the invention includes a converter 50 controllable from a control input 51, the converter being suitable for transforming an electrical signal into an audible signal, and a fifth electrical connector 52 for connecting the control terminal 51 of the converter 50 to the output 37 of the electronic control circuit that is suitable for delivering an alarm signal. In highly advantageous manner, there are also provided means for applying the second alarm signal issued by the flow rate regulator circuit to the control terminal 51 of the converter 50.

In an embodiment that is particularly advantageous in the ambit of the invention, the converter 50 is situated in the duct 14 and it is constituted by at least one of the following elements: a buzzer, a loudspeaker, etc.

Provision is also made for the ventilator unit to include means 18 for establishing a fluid connection between the end 19 of the duct 14 that is situated on the outside 15 of the first case 1 and an inlet for feeding ventilation fluid to the inside of the garment. These means are represented in highly diagrammatic form in the sole FIGURE, being known in themselves, and possibly being constituted by a screw coupling and a gasket, for example.

The above-described ventilator unit operates as follows:

It is assumed that it is necessary to ventilate the inside of a pressure suit for the comfort of the person wearing the suit, and also so as to allow that person to breathe air normally at a determined pressure, generally slightly higher than the pressure of the atmosphere, with the breathed-in air being exempt of any particles that are harmful to health.

For this purpose, the above-described ventilator unit situated outside the garment to be ventilated is connected by the means 18 to an admission sleeve with which any such pressure suit is generally provided, and then the control element 42 of the switch 40 is actuated.

Under the effect of this instruction, the electronic control circuit 26 connects the output 24 of the energy source 23 to the power supply input 11 of the motor 10, via the connector 33 in particular.

Rotation of the motor puts the impeller 7 into operation so that it sucks in air from the outside medium 15 via its inlet ports 8, which air passes through the filter cartridges 5 and the inside 13 of the first case, and it delivers the air via its outlet orifice 9 so as to blow the air into the inside of the suit via the duct 14 and the connection means 18.

When air flows along the duct 14, it drives the flow meter 29 which delivers a signal to its output 30 that is representative of the flow rate of air traveling along the duct. This signal is applied to the input 32 of the electronic control circuit 26 which compares it with a reference signal as stored in the circuit and representing the value of a minimum reference flow rate and/or a maximum reference flow rate. Depending on the result of the comparison, the electronic control circuit can issue an instruction to the power supply input 11 of the motor 10 via the connector 33 so as to cause the motor to turn at an appropriate speed and produce the desired air flow rate in the duct 14.

The ventilator unit can thus operate throughout the time needed to ventilate the inside of the suit to ensure the safety of the person wearing it.

Nevertheless, incidents can occur, for example a drop in the voltage at the output 24 of the energy source 23. Under such circumstances, the electronic control circuit 26 issues the first alarm signal via its output 37 so as to control the converter 50 and warn the person wearing the suit that an incident is about to occur in the operation of the ventilator unit.

The same applies when the flow rate regulator circuit finds that the fluid flow rate is too high or too low. Under such circumstances, the second alarm signal is issued so as to operate the converter 50 in the same manner as that described above.

It should be observed that this ventilator unit presents an important advantage constituted by the fact that the converter 50, advantageously constituted by a buzzer, is situated in the duct 14, so the person wearing the suit is warned very quickly of an approaching incident and in a manner that is more reliable than with prior art devices since the ventilation air passing along the duct 14 immediately conveys the noise of the buzzer to the inside of the suit and to the hearing system of the person wearing the suit.

With the ventilator unit of the invention, it is possible by means of the electrical connection pin 22 mounted in leaktight manner through the wall 49 of the second case 20, to recharge the source 23 electrically when it is constituted by rechargeable batteries, and also to modify the program of the electronic control circuit 26 so as to adapt it to the conditions in which the ventilator unit is used and to the nature of the elements making it up, for example the nature of the energy source 23, of the flow meter 29, and of the alarm.

The invention claimed is:

1. A ventilator unit for ventilating the inside of a garment such as a pressure suit or the like with an ambient fluid, the unit being characterized by the fact that it comprises:

a first leaktight case (1) having at least one inlet opening (2) suitable for sucking in said fluid, and an outlet opening (3), and also a first electrical connection passage (4);

a filter cartridge (5);

means (6) for mounting the filter cartridge (5) in association with the inlet opening (2) of the first case (1);

an impeller (7) having at least one inlet port (8) for sucking in said fluid contained in said first case (1), and an outlet orifice (9) for delivering said sucked-in fluid, said impeller (7) having a drive motor (10) controllable via a power supply input (11);

means (12) for mounting said impeller (7) in the inside (13) of the first case (1);

a duct (14) for connecting the outlet orifice (9) of the impeller (7) to the outside (15) of the first case (1), said duct (14) passing in leaktight manner through the outlet opening (3) of the first case (1);

a second case (20);

a second electrical connection passage (21) made through the wall (49) of said second case (20);

a source (23) suitable for delivering electrical energy to an output terminal (24), said source (23) being disposed in the inside (25) of the second case (20);

an electronic control circuit (26);

means (27) for associating the first and second cases (1, 20) in such a manner that the first and second electrical connection passages (4, 21) form a single leakproof third electrical connection passage (28);

a flow meter (29) disposed inside the duct (14), said flow meter having an outlet (30) suitable for delivering an electrical signal representative of the flow rate of fluid passing along the duct (14);

a first electrical connector (31) for connecting the output (30) of the flow meter (29) to a first input (32) of the electronic control circuit (26);

a second electrical connector (33) for connecting a first control output (34) of the electronic control circuit (26) to the control input (11) of the motor (10) for driving the impeller; and a third electrical connector (35) for connecting the electrical energy source (23) to a power supply input (36) of the electronic control circuit (26);

said electronic control circuit (26) further including an output (37) suitable for delivering a first alarm signal when the level of electrical energy delivered by said source (23) drops below a determined threshold value, a converter controllable from a control input (51), said converter being adapted to transform an electrical signal into a sound signal; and a fifth electrical connector (52) for connecting the control terminal (51) of the converter (50) to that output (37) of the electronic control circuit that is adapted to deliver said first alarm signal, said converter (50) being situated in said duct (14) so that the converter (50) is directly inside the fluid flowing in the duct.

2. A ventilator unit according to claim 1, characterized by the fact that said electronic control circuit (26) is located inside the second case (20).

3. A ventilator unit according to claim 2, characterized by the fact that it includes an electrical connection pin (22) mounted in leaktight manner through the wall (49) of the second case (20), the output terminals (46) thereof being situated in the inside (25) of said second case (20) and being connected respectively to an energy feed input (47) of said energy source (23) and to a control input (48) of the electronic control circuit (26).

4. A ventilator unit according to claim 2, characterized by the fact that it further comprises:

a switch (40) mounted in leaktight manner through the wall (41) of the first case (1) so that its control element (42) is accessible from the outside (15) of the first case (1) and its electrical control terminals (43) are situated in the inside (13) of the first case (1); and a fourth electrical connector (44) for connecting the electrical control terminals (43) of said switch (40) to a control input (45) of the electronic control circuit (26).

5. A ventilator unit according to claim 4, characterized by the fact that it includes an electrical connection pin (22) mounted in leaktight manner through the wall (49) of the second case (20), the output terminals (46) thereof being situated in the inside (25) of said second case (20) and being connected respectively to an energy feed input (47) of said energy source (23) and to a control input (48) of the electronic control circuit (26).

6. A ventilator unit according to claim 1, characterized by the fact that it further comprises:

a switch (40) mounted in leaktight manner through the wall (41) of the first case (1) so that its control element (42) is accessible from the outside (15) of the first case (1) and its electrical control terminals (43) are situated in the inside (13) of the first case (1); and a fourth electrical connector (44) for connecting the electrical control terminals (43) of said switch (40) to a control input (45) of the electronic control circuit (26).

7. A ventilator unit according to claim 6, characterized by the fact that it includes an electrical connection pin (22) mounted in leaktight manner through the wall (49) of the second case (20), the output terminals (46) thereof being situated in the inside (25) of said second case (20) and being connected respectively to an energy feed input (47) of said energy source (23) and to a control input (48) of the electronic control circuit (26).

8. A ventilator unit according to claim 1, characterized by the fact that said converter (50) is constituted by at least one of the following elements: a buzzer, a loudspeaker.

9. A ventilator unit according to claim 1, characterized by the fact that said filter cartridge (5) is constituted:

by a filter pellet (60) for filtering first particles of a given size, said pellet (60) covering said inlet opening (2) of the first case (1) in full; and a cap (61) covering said pellet (60) in such a manner that the pellet is situated between the cap and the inlet opening (2) of the first case, said cap including filter orifices (62) for filtering second particles of a size greater than the size of the first particles.

10. A ventilator unit according to claim 1, characterized by the fact that it includes means (18) for making a fluid connection between the end (19) of said duct (14) situated outside said first case (1) with an inlet for feeding the inside of said garment with fluid.

11. A ventilator unit according to claim 1, characterized by the fact that it includes a flow regulator circuit suitable for delivering a second alarm signal when the fluid flow rate in the duct (14) varies by a determined quantity about a given nominal flow rate value.

12. A ventilator unit according to claim 11, characterized by the fact that said flow rate regulator circuit is disposed in said first case (1).

13. A ventilator unit according to claim 11, characterized by the fact that it includes means for applying said second alarm signal to the control terminal (51) of said converter (50).

14. A ventilator unit according to claim 13, characterized by the fact that said flow rate regulator circuit is disposed in said first case (1).

15. A ventilator unit according to claim 1, characterized by the fact that said converter (50) is constituted by at least one of the following elements: a buzzer, a loudspeaker.

16. A ventilator unit according to claim 1, characterized by the fact that it includes a flow regulator circuit suitable for delivering a second alarm signal when the fluid flow rate in the duct (14) varies by a determined quantity about a given nominal flow rate value.

* * * * *